(12) United States Patent
Küng et al.

(10) Patent No.: US 6,534,533 B2
(45) Date of Patent: Mar. 18, 2003

(54) FUNGICIDAL COMPOSITIONS BASED ON METALAXYL

(75) Inventors: Ruth Beatrice Küng, Allschwil (CH); Micha Wicki, Arlesheim (CH); Cosima Nuninger, Colmar (FR); Martin Weiss, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/954,313

(22) Filed: Sep. 13, 2001

(65) Prior Publication Data

US 2002/0099052 A1 Jul. 25, 2002

Related U.S. Application Data

(62) Division of application No. 09/380,363, filed as application No. PCT/EP98/01189 on Mar. 3, 1998, now Pat. No. 6,313,121.

(30) Foreign Application Priority Data

May 3, 1997 (CH) ................................................ 520/97

(51) Int. Cl.$^7$ ......................... A01N 43/76; A01N 37/12; A01N 37/44
(52) U.S. Cl. ........................................ 514/376; 514/538
(58) Field of Search ................................. 514/326, 538

(56) References Cited

FOREIGN PATENT DOCUMENTS

| EP | 0 280 348 | 8/1988 |
|---|---|---|
| GB | 2 213 063 | 8/1989 |
| WO | WO 96 01559 | 1/1996 |
| WO | WO 96 01560 | 1/1996 |

*Primary Examiner*—Allen J. Robinson
(74) *Attorney, Agent, or Firm*—William A. Teoli, Jr.; Rose M. Allen

(57) ABSTRACT

Metalaxyl having a high content of R-enantiomer of more than 70% by weight, or pure R-metalaxyl, in admixture with 4-[3-(4-chlorophenyl)-3-(3,4-dimethoxyphenyl)acryloyl]-morpholine ("dimethomorph") or 3-anilino-5-methyl-5-(4-phenoxyphenyl)-1,3-oxazolidine-2,4-dione ("famoxadone"), exhibits a clearly enhanced fungicidal action against plant diseases compared with a mixture of the same kind in which metalaxyl is used in the form of a racemate.

13 Claims, No Drawings

FUNGICIDAL COMPOSITIONS BASED ON METALAXYL

This is a divisional application of Ser. No. 09/380,363, filed on Aug. 31, 1997, now U.S. Pat. No. 6,313,121 which is a 371 of PCT/EP98/01189, filed Mar. 3, 1998.

The present invention relates to fungicidal two-component mixtures having an unexpectedly enhanced activity that are based on metalaxyl having an R-enantiomer content of more than 70% by weight, and to the use of those mixtures in the control and prevention of infestation by Oomycetes. The metalaxyl component is referred to as active ingredient I.

The mixing partner 11 is one of the following fungicides:

IIA) 4-[3-(4-chlorophenyl)-3-(3,4-dimethoxyphenyl) acryloyl]morpholine ("dimethomorph") (The Pesticide Manual, 10$^{th}$ Ed., pages 351–2, 1994), or IIB) 3-anilino-5-methyl-5-(4-phenoxyphenyl)-1,3-oxazolidine-2,4-dione ("famoxadone") (Brighton Crop Protection Conference, Pests & Diseases 1996, Vol. I, pages 21–26). It is also possible to use salts or metal complexes of compounds IIA or IIB, for example copper or manganese salts.

In the narrower sense, the invention relates to mixtures of pure metalaxyl having an R-enantiomer content of more than 85% by weight, especially more than 92% by weight, or more especially more than 95% by weight. The best results are achieved with pure R-enantiomer that is substantially free of S-enantiomer.

Metalaxyl is methyl N-(2,6-dimethylphenyl)-N-(methoxyacetyl)-DL-alaninate and has the structure

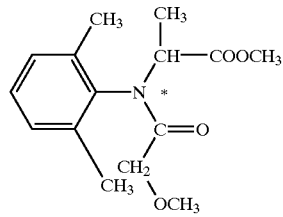

It has an asymmetrical *C atom and can be separated into the enantiomers in conventional manner (GB-1 500 581). Since 1975 it has been known by experts in the field that the fungicidal action of the R-enantiomer far exceeds that of the S-enantiomer, and the R-enantiomer is in practice considered to form the true active principle. Commercial metalaxyl is available in the form of a racemate. A need to resolve the racemate, half of which consists of the desired R-enantiomer, has never arisen in the past for practical reasons.

Completely surprisingly, it has now been found that R-metalaxyl in pure form, or in a form concentrated to more than 70% in the racemate, in co-operation with one of the fungicidal partners IIA or IIB, achieves unexpectedly high enhanced effects, some of which exceed the effects of the racemate-based mixtures (for example mentioned in EP-280 348 or EP-393 911) by factors of up to 10. Factors that might have been expected, based on the R-enantiomer content of th e racemate being approximately 50%, would be 2 at most.

With this completely unexpected result, the present invention represents a very substantial enrichment of the art and a possibility of reducing the total rates of application of fungicides used in the control of Oomycetes on plants, thereby safeguarding the environ ment. The dramatically improved degradability of metalaxyl in the soil as soon as the R -enantiomer content exceeds 70% by weight is known from WO-96/01559.

In addition to the two-component mixture I:II, the present invention relates also to a method of controlling fungi which comprises treating a site, for example a plant, infested by or at risk of infestation by fungi with a) component I and b) the compound II in any order or simultaneously.

Favourable I:II mixing ratios of the two compounds are from 30:1 to 1:30, especially from 10:1 to 1:10, more especially from 10:1 to 1:5. In many cases, mixtures in which the mixing ratio of compound I to compound II is from 1:1 to 1:5 are advantageous.

The compound mixtures I+II according to the invention have very advantageous curative, preventive and systemic fungicidal properties for the protection of cultivated plants. With the compound mixtures of the invention it is possible to inhibit or destroy the microorganisms that occur on plants or parts of plants (the fruit, blossom, leaves, stems, tubers or roots) of various crops of useful plants, while the parts of plants that grow later are also protected from such microorganisms. This applies especially also to microorganisms that have developed reduced sensitivity to metalaxyl.

The mixtures of compounds I and II are usually used in the form of compositions. R-metalaxyl (I) and the compound II may be applied simultaneously or directly one after the other to the area or plant to be treated, if desired together with further carriers, surfactants or other application-promoting additives that are customary in formulation technology.

Suitable carriers and additives may be solid or liquid and are substances that are expedient in formulation technology, for example natural or regenerated mineral substances, solvents, dispersing agents, wetting agents, tackifiers, thickening agents, binders or fertilisers.

A preferred method of applying a compound mixture that comprises at least one each of the compounds I and II is application to the parts of the plant above the soil, especially the leaves (foliar application). The frequency and rate of application depend on the biological and climatic living conditions for the pathogen in question. The compounds may also penetrate the plant through the root system via the soil (systemic action) as a result of impregnation of the locus of the plant with a liquid preparation or by means of introduction of the compounds into the soil in solid form, for example in the form of granules (soil application).

The compounds of the combination are used in unmodified form or preferably together with the adjuvants conventionally employed in formulation technology and are accordingly formulated in known manner, for example, into emulsifiable concentrates, coatable pastes, directly sprayable or dilutable solutions, dilute emulsions, wettable powders, soluble powders, dusts or granules, or by encapsulation in substances, for example polymeric substances. As with the nature of the compositions, the methods of application, such as spraying, atomising, dusting, scattering, coating or pouring, are chosen in accordance with the intended objectives and the prevailing circumstances. Favourable rates of application of the compound mixture are generally from 50 g to 1800 g of active ingredient (a.i.) per hectare (ha), especially from 100 g to 1000 g a.i./ha.

The formulations are prepared in known manner, e.g. by intimately mixing and/or grinding the active ingredients with extenders, such as solvents, solid carriers and, where appropriate, surface-active compounds (surfactants).

The agrochemical compositions usually contain 0.1 to 99% by weight, especially 0.1 to 95% by weight of compounds of formulae I and II, 99.9 to 1% by weight, especially 99.9 to 5% by weight of a solid or liquid adjuvant, and 0 to 25% by weight, especially 0.1 to 25% by weight of a surfactant.

Whereas commercial products are preferably formulated as concentrates, the end user will normally employ dilute formulations.

Suitable target crops are especially potatoes, vines, hops, maize, sugar beet, tobacco, vegetables (tomatoes, paprika, lettuce etc.), and also bananas, rubber, lawn grasses and ornamental plants. Other plants endangered by downy mildew are known, inter alia, from the literature on metalaxyl.

The following Examples serve to illustrate the invention, "active ingredient" denoting a mixture of metalaxyl (having an R-metalaxyl content of more than 95% by weight) and compound II in a particular mixing ratio.

| Wettable powders | a) | b) | c) |
|---|---|---|---|
| active ingredient [I:IIA = 1:1(a), 1:10(b); I:IIB = 1:5(c)] | 26% | 44% | 72% |
| sodium lignosulfonate | 5% | 5% | — |
| sodium lauryl sulfate | 3% | — | 5% |
| sodium diisobutylnaphthalene sulfonate | — | 6% | 10% |
| octylphenol polyethylene glycol ether (7–8 mol of ethylene oxide) | — | 2% | — |
| highly dispersed silicic acid | 6% | 13% | 13% |
| kaolin | 60% | 30% | — |

The active ingredient is mixed thoroughly with the adjuvants and the mixture is thoroughly ground in a suitable mill, affording wettable powders which can be diluted with water to give suspensions of any desired concentration.

| Emulsifiable concentrate | |
|---|---|
| active ingredient (I:IIA or IIB = 2:1) | 12% |
| Octylphenol polyethylene glycol ether (4–5 mol of ethylene oxide) | 3% |
| calcium dodecylbenzenesulfonate | 3% |
| castor oil polyglycol ether (35 mol of ethylene oxide) | 4% |
| cyclohexanone | 30% |
| xylene mixture | 48% |

Emulsions of any desired dilution that can be used in plant protection can be obtained from this concentrate by dilution with water.

| Extruder granules | |
|---|---|
| active ingredient (I:IIA = 1:1) | 16% |
| sodium lignosulfonate | 2% |
| carboxymethylcellulose | 1% |
| kaolin | 81% |

The active ingredient is mixed and ground with the adjuvants, and the mixture is moistened with water. The mixture is extruded and then dried in a stream of air.

| Coated granules | |
|---|---|
| active ingredient (I:IIB = 10:1) | 11% |
| polyethylene glycol (mol. wt. 200) | 3% |
| kaolin | 86% |

The finely ground active ingredient is uniformly applied, in a mixer, to the kaolin moistened with polyethylene glycol. Non-dusty coated granules are obtained in this manner.

| Suspension concentrate | |
|---|---|
| active ingredient (I:IIA or IIB = 1:10) | 44% |
| propylene glycol | 10% |
| nonylphenol polyethylene glycol ether (15 mol of ethylene oxide) | 6% |
| sodium lignosulfonate | 10% |
| carboxymethylcellulose | 1% |
| silicone oil (in the form of a 75% aqueous emulsion) | 1% |
| water | 28% |

The finely ground active ingredient is intimately mixed with the adjuvants, giving a suspension concentrate from which suspensions of any desired dilution can be obtained by dilution with water. Using such dilutions, living plants can be treated and protected from a infestation by microorganisms by spraying, watering or immersion.

BIOLOGICAL EXAMPLES

Example 1

Action Against Plasmopara Viticola on Vines

Vine seedlings of the Gutedel variety are grown under greenhouse conditions (20–24° C.) to the 4- to 5-leaf stage (3 weeks). Disks I0 mm in diameter are then cut from the leaves. The leaf segments are placed on Petri dishes with their upper side facing downwards. The dishes contain 1.8 ml water/0.16% agar. The fungicides are added to demineralised water and diluted appropriately. The fungicidal treatment is carried out one day before the inoculation. The entire leaf surface disk is then uniformly sprayed to drip point with a freshly prepared sporangia suspension (50 000–60 000/ml) of *Plasmopara viticola*. The plants are subsequently kept in a controlled environment chamber for 7 days at 18° C. and approximately 100% relative humidity with artificial daylight of 12 hours' duration (3000 lux). Evaluation of the infestation is then carried out.

The percentage leaf infestation is assessed and the percentage action relative to the control is calculated. The comparison between the percentage action of the mixture R-metalaxyl (>95% by weight)/famoxadone and the mixture metalaxyl(rac.)/famoxadone gives the comparison factor.

| R-metalaxyl >95% by wt. or metalaxyl (racemate) mg a.i./l | Famoxadone mg a.i./l | Mixing ratio I:II | Activity of R-metalaxyl (95%) plus famoxadone % | Activity of metalaxyl (rac.) plus famoxadone % | Comparison factor |
|---|---|---|---|---|---|
| 0.1 | 0.1 | 1:1 | 29.1 | 3.1 | 9.5 |
| 0.1 | 0.5 | 1:5 | 52.7 | 14.9 | 3.5 |
| 0.1 | 1 | 1:10 | 52.7 | 22.0 | 2.4 |

Example 2

Action Against Phytophthora Infestans on Tomatoes

Tomato plants of the variety cv.Baby are grown individually in flower pots (diameter=8 cm) under greenhouse conditions for 4 weeks. The plants are then sprayed with active ingredient formulation prepared from an emulsifiable concentrate. 3 plants are used in each case. The entire leaf surface of the lower leaves of the plant are then uniformly sprayed with a freshly prepared sporangia suspension (80 000/ml) of *Phytophthora infestans*. The plants are subsequently kept for 2 days at 15° C. and approximately 100% relative humidity with artificial daylight of 16 hours' duration and then for a further 5 days at 15° C. and 60% relative humidity. Evaluation of the infestation is then carried out. The percentage leaf infestation is assessed and the percentage action relative to the control is calculated. The comparison between the percentage action of the mixture R-metalaxyl (>95% by weight)/dimethomorph and the mixture metalaxyl (rac.)/dimethomorph gives the comparison factor.

| R-metalaxyl >95% by wt. or metalaxyl racemate mg a.i./l | Dimethomorph mg a.i./l | Mixing ratio I:II | Activity of R-metalaxyl (95%) plus dimethomorph % | Activity of metalaxyl (rac.) plus dimethomorph % | Comparison factor |
|---|---|---|---|---|---|
| 0.25 | 0.25 | 1:1 | 86.0 | 16.0 | 5.3 |
| 0.25 | 0.5 | 1:2 | 87.0 | 39.0 | 2.2 |

What is claimed is:

1. A fungicidal two-active agent component composition based on metalaxyl (1), wherein more than 70% by weight of the metalaxyl consists of the R-enantiomer and the composition comprises as a further component IIB) 3-anilino-5methyl-5-(4-phenoxyphenyl)-1,3-oxazolidine-2,4-dione ("famoxadone") or a salt or a metal complex thereof, in synergistic effective amounts together with a suitable carrier, wherein said I and II are present in a weight ratio of I:IIB of at least 1:30 and are present in a weight ratio not exceeding 30:1.

2. The composition according to claim 1, wherein the ratio by weight of I:IIB Is at least 1:10.

3. The composition according to claim 1, wherein the metalaxyl has an R-enantiomer content of more than 85% by weight.

4. The composition according to claim 3, wherein the metalaxyl has an R-enantiomer content of make than 92% by weight.

5. The composition according to claim 4, wherein said metalaxyl is substantially pure R-metalaxyl that is substantially free of S-metalaxyl.

6. The composition according to claim 1, wherein the ratio by weight of I:IIB Is not more than 10:1.

7. The composition according to claim 4, wherein the metalaxyl has an R-enantiomer content of more than 95% by weight.

8. A method of controlling and preventing the infestation of plants, parts of plants or their growing site by Oomycetes, which comprises applying synergistic effective amounts simultaneously or directly one after the other in any order, metalaxyl having an R-enantiomer content of more than 70% by weight and famoxadone (IIB) and are applied at rates such that the combined active agent weight of I and IIB is at least 50 g per hectacre and I and IIB are used in an active agent weight ratio of I:IIB of at least 1:30 and said ratio is not more than 30:1.

9. The method according to claim 8, wherein said metalaxyl has an R-enantiomer content of more than 85% by weight.

10. The method according to claim 9, wherein said metalaxyl is substantially pure R-metalaxyl that is substantially free of S-metalaxyl.

11. The method according to claim 9 wherein Phytophthora spp, Plasmopara, Pythium, Pseudoperonospora, Albugo occidental is and/or Bremia are controlled.

12. The method of claim 9 wherein said compound I and compound IIB are applied at rates such that the combined active agent weight of I and IIB is not more than 1800 g per hectacre.

13. The method according to claim 9, wherein said metalaxyl has an R-enantiomer content of more than 92% by weight.

* * * * *